United States Patent [19]

Maeda et al.

[11] Patent Number: 5,507,767
[45] Date of Patent: Apr. 16, 1996

[54] SPIRAL STENT

[75] Inventors: Munehiro Maeda, Yamato-Takada, Japan; Hans A. Timmermans, Portland, Oreg.; Barry T. Uchida, Lake Grove, Oreg.; Josef Rösch, Portland, Oreg.

[73] Assignee: Cook Incorporated, Bloomington, Ind.

[21] Appl. No.: 821,477

[22] Filed: Jan. 15, 1992

[51] Int. Cl.⁶ ................................................ A61M 29/00
[52] U.S. Cl. .............................. 606/198; 623/1; 623/12
[58] Field of Search ................................. 606/108, 191, 606/198, 200; 623/1, 12

[56] References Cited

U.S. PATENT DOCUMENTS

| | | |
|---|---|---|
| 4,512,338 | 4/1985 | Balko et al. . |
| 4,553,545 | 11/1985 | Maass et al. . |
| 4,580,568 | 4/1986 | Gianturco . |
| 4,649,922 | 3/1987 | Wiktor . |
| 4,655,771 | 4/1987 | Wallsten . |
| 4,665,918 | 5/1987 | Garza et al. . |
| 4,800,882 | 1/1989 | Gianturco . |
| 4,820,298 | 4/1989 | Leveen et al. . |
| 4,830,003 | 5/1989 | Wolff et al. . |
| 4,856,516 | 8/1989 | Hillstead . |
| 4,878,906 | 11/1989 | Lindemann et al. . |
| 4,886,062 | 12/1989 | Wiktor . |
| 4,954,126 | 9/1990 | Wallsten . |
| 4,969,458 | 11/1990 | Wiktor . |
| 5,015,253 | 5/1991 | MacGregor . |
| 5,019,090 | 5/1991 | Pinchuk . |
| 5,026,377 | 6/1991 | Burton . |
| 5,035,706 | 7/1991 | Gianturco et al. . |
| 5,041,126 | 8/1991 | Gianturco . |
| 5,133,732 | 7/1992 | Wiktor ................................. 623/1 |
| 5,282,824 | 2/1994 | Gianturco ......................... 606/198 |
| 5,290,305 | 3/1994 | Inoue ............................... 606/191 |

FOREIGN PATENT DOCUMENTS

| | | |
|---|---|---|
| 0183372 | 6/1986 | European Pat. Off. . |
| 0312852 | 4/1989 | European Pat. Off. . |
| 2135585 | 10/1983 | United Kingdom . |

Primary Examiner—Stephen C. Pellegrino
Assistant Examiner—William W. Lewis
Attorney, Agent, or Firm—Woodard, Emhardt, Naughton, Moriarty & McNett

[57] ABSTRACT

A self-expanding endovascular stent formed of stainless steel wire which is bent into an elongated zigzag pattern. The zigzag pattern has a plurality of substantially straight wire sections of various lengths separating a plurality of bends. The zigzag pattern is helically wound about a central axis to define a tubular shape such that a majority of the bends are disposed in a helix. Adjacent bends in the helix are interconnected with a filament. The stent is capable of being radially compressed such that the straight wire sections and the bends are tightly packed around a central axis. The stent resiliently self-expands to assume a tubular shape when released from the compressed state. Depending on the pattern of the lengths of the straight wire sections in the zigzag pattern, the final tubular shape can be made irregular to match a patient's vascular system. In other words, the diameter of the tube which is defined by the stent can be made to vary along the length of the stent. Stents of the present invention are used to expand a passageway, hold a passageway open, or create a passageway.

10 Claims, 4 Drawing Sheets

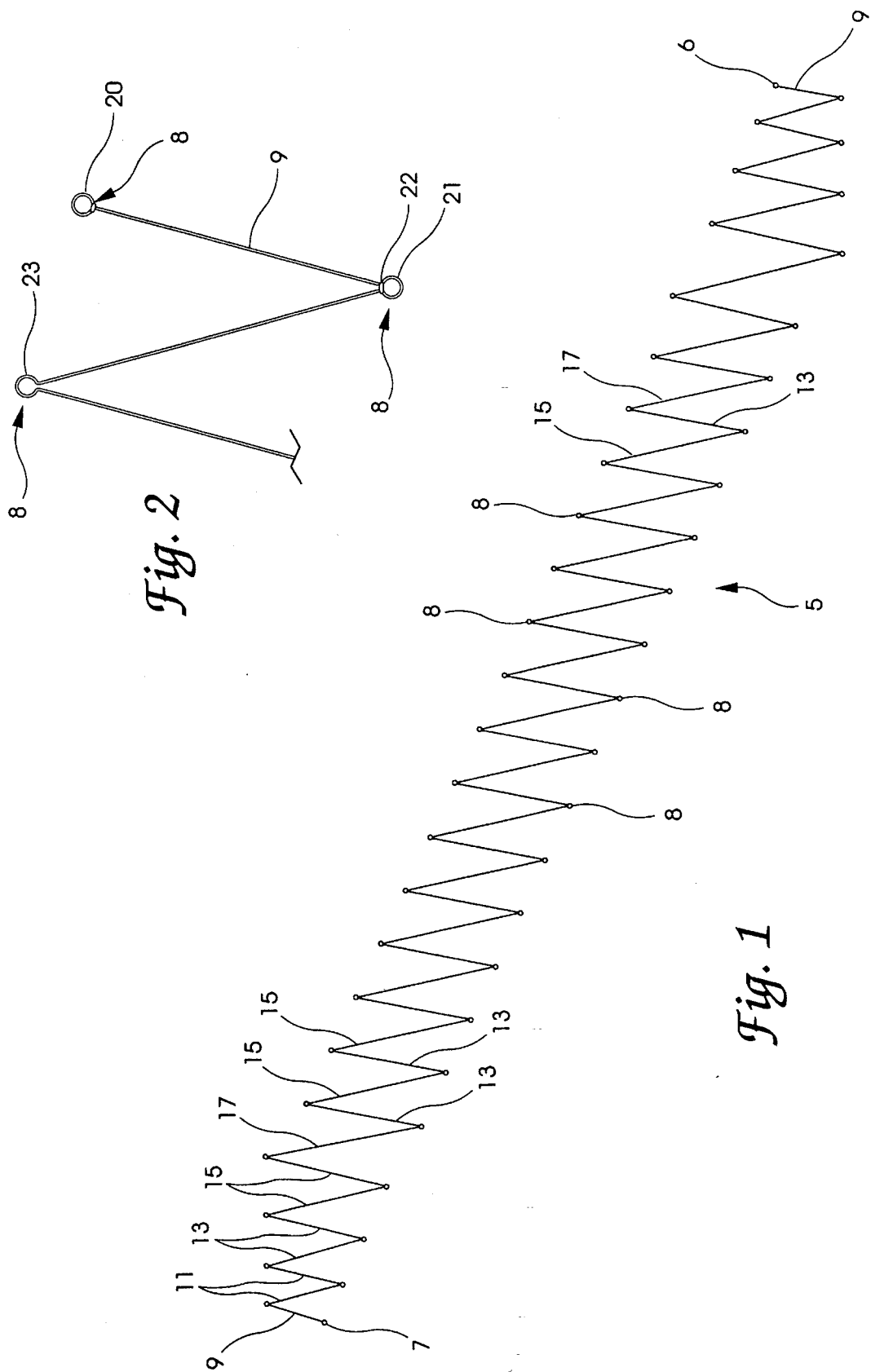

SPIRAL STENT

BACKGROUND OF THE INVENTION

This invention relates generally to self-expanding endovascular stents for use in preventing restenosis of passageways and ducts in the body, to repair aneurysms percutaneously, and also for dilating recurring stenosis immediately after attempts with ballooning.

This invention represents an improvement in the self-expanding stents described and shown in U.S. Pat. No. 4,580,568 to Gianturco. Conventional stents of this type include a wire formed in a closed zigzag configuration that includes an endless series of straight sections joined by bends. A conventional zigzag stent is resiliently compressible into a small diameter such that the straight sections are arranged side by side and closely adjacent one another for insertion into a passageway. The stent is resiliently self-expandable into a larger second diameter wherein the straight sections press against the walls of the passageway to maintain it open. Although conventional zigzag stents have proven quite useful in many situations, their performance characteristics tend to decrease as the length of the stent increases.

Self-expanding stents are normally evaluated with respect to four performance characteristics: the radially outward expansile force that the stent exerts on the vascular wall; the small diameter to which the stent is capable of being compressed for the insertion procedure; the ability of the stent to adapt to curved passageways in the patient's body; and the stability of the stent in not migrating from its originally implanted position within the patient.

Conventional zigzag stents must normally be made relatively short because the straight wire sections prevent the stent from readily adapting to curves in the passageway of a patient. Furthermore, the expansile force of conventional zigzag stents generally decreases with the length of the stent. One solution to these drawbacks has been to modify the conventional zigzag stent by connecting a plurality of shorter stents end on end to create one longer zigzag stent assembly. Although these modified zigzag stents represent an improvement over conventional zigzag stents for certain applications, there exists a need for an elongated self-expanding stent that includes the advantages of both conventional and modified zigzag stents but which has improved performance characteristics over both.

The present invention also represents an improvement over the self-expanding spiral stents described in U.S. Pat. No. 5,019,090 to Pinchuk. Pinchuk teaches the production of an elongated zigzag pattern by spirally wrapping a wire about an oblong mandrel, removing the mandrel, and then flattening the spiral to produce an elongated zigzag band. The elongated zigzag band is then spirally wrapped around a cylindrical mandrel to produce the stent. One drawback to the Pinchuk design, however, is that all of the elongate member's that make up the zigzag pattern have equal lengths. The result being that a bisector of the angle defined by each pair of elongated members is not parallel to the central axis of the finished stent. This causes the stent to undesirably distort in shape when radially compressed for the implantation procedure. What is needed is a spiral zigzag stent in which a bisector of each pair of elongated members is parallel to the central axis of the finished stent. Such a stent cannot be produced by the method for making stents taught by Pinchuk.

SUMMARY OF THE INVENTION

The preferred embodiment of the present invention includes a wire bent into an elongated zigzag pattern having a plurality of substantially straight wire sections separating a plurality of bends. The elongated zigzag pattern is helically wound about a central axis to define a tubular shape such that a majority of the plurality of bends are disposed in a helix. Means are provided for interconnecting adjacent bends of the helix. The stent has the capability of being radially compressed into a small-diameter shape such that the straight wire sections and the bends are tightly packed around the central axis of the tubular shape. The stent will resiliently self expand to assume the tubular shape when released from the compressed state.

One object of the present invention is to provide an elongated self-expanding stent having substantially uniform expansile force along the length of the stent.

Another object of the present invention is to provide a self-expanding stent which may be compressed into a small diameter for improved percutaneous insertability.

Still another object of the present invention is to provide an elongated self-expanding stent which has a substantially uniform capability along its length to adapt to curves in the vascular system where the stent is implanted.

Another object of the present invention is to provide a stent which has improved stability in maintaining its position within the patient.

Finally, it is an object of the present invention to provide an improved self-expanding stent.

Related objects and advantages of the present invention will be apparent from the following description.

BRIEF DESCRIPTION OF THE DRAWINGS

FIG. 1 is a plan view showing a wire bent into an elongated zigzag pattern.

FIG. 2 is an enlarged view of one end of the zigzag pattern of FIG. 1.

DESCRIPTION OF THE PREFERRED EMBODIMENT

Figure 3:
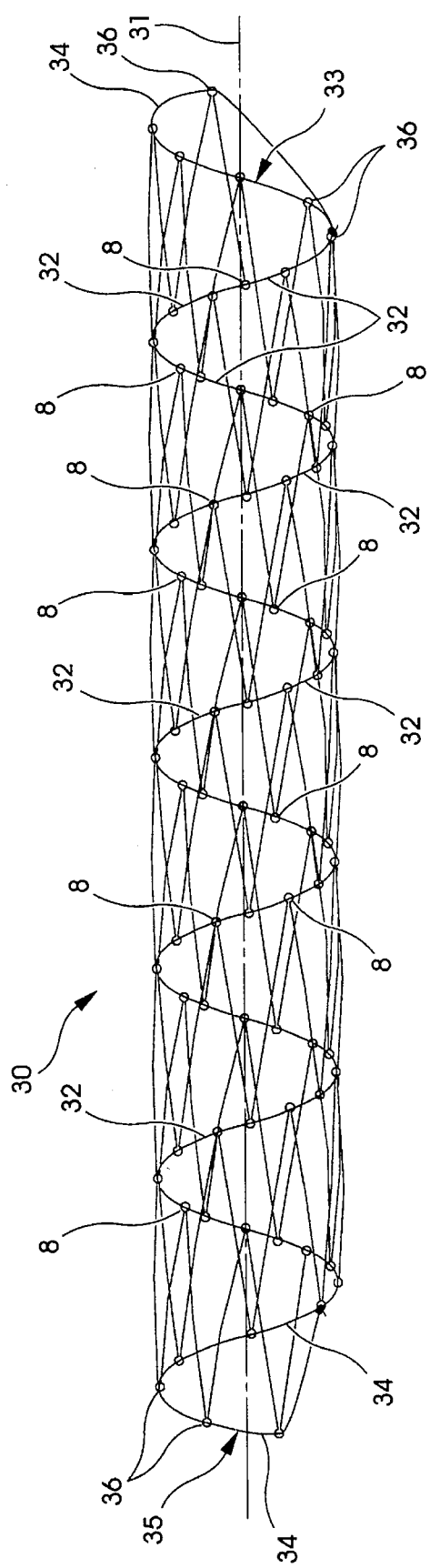
FIG. 3 is a side elevation of the preferred embodiment of the present invention in its expanded state.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to the drawings, there is illustrated in FIG. 1 a midpoint in the construction of the stent which comprises the preferred embodiment of the present invention. FIG. 1 shows a wire bent into an elongated zigzag pattern 5 having a plurality of substantially straight wire sections 9–15 of various lengths separated by a plurality of bends 8. The wire has first and second ends designated as 6 and 7, respectively. Zigzag pattern 5 is preferably formed from a single strand of stainless steel wire having a diameter in the range of 0.005 to 0.025 inch.

Figure 4:
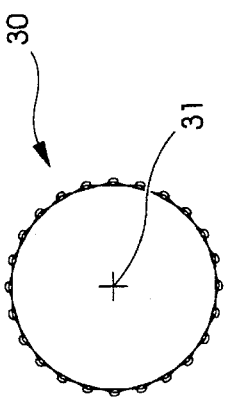
FIG. 4 is an end view of the stent of FIG. 3.
Figure 5:
FIG. 5 is a side elevation of the preferred embodiment of the present invention in its compressed state.

FIG. 3 shows a completed stent 30 according to the preferred embodiment of the present invention. The construction of the stent is completed by helically winding elongated zigzag pattern 5 about a central axis 31. Zigzag pattern 5 is wound in such a way that a majority of the bends 8 are distributed in a helix along the length of the stent 30. There are preferably about twelve interconnected bends in each revolution of the helix, or six adjacent bends of the zigzag pattern in each revolution. The construction of stent 30 completed by interconnecting adjacent bends of the helix with a filament 32, preferably a nylon monofilament suture. Filament 32 acts as a limit means to prevent the stent from further radial expansion beyond the tubular shape shown in FIGS. 3 and 4. The tubular shape has a central axis 31, a first end 33 and a second end 35. Each end of stent 30 is defined by a plurality of end bends 36, which are themselves interconnected with a filament 34. Other embodiments of the present invention are contemplated in which the end bends 36 are left unconnected in the finished stent. FIG. 4 shows an end view of stent 30 further revealing its tubular shape. FIG. 5 shows stent 30 of FIG. 3 when radially compressed about central axis 31 such that the straight wire sections and the bends are tightly packed around central axis 31.

Referring back to FIG. 1, the zigzag pattern is made up of straight wire sections having various lengths which are distributed in a certain pattern to better facilitate the helical structure of the final stent construction. instance, in one embodiment, end wire sections 9 could be made to a length of 9 mm followed by two wire sections 11 each being 11 mm in length. Wire sections 11 are followed by two 13 mm wire sections 13, which are in turn followed by two wire sections 15 having a length of 15 mm. Sections 15 are followed by a single wire section 17 having a length of 17 mm. These gradually increasing wire sections at either end of the zigzag pattern enable the final stent to have well defined square ends. In other words, the gradually increasing length wire sections on either end of the zigzag pattern enable the final stent to have a tubular shape in which the ends of the tube are substantially perpendicular to the central axis of the stent. Following wire section 17, there are a plurality of alternating length sections 13 and 15. Short sections 13 being 13 mm in length add long sections 15 being 15 mm in length. This alternating sequence is continued for whatever distance is desired to correspond to the desired length of the final stent. The difference in length between the short sections 13 and long sections 15 is primarily dependent upon the desired slope of the helix (see β in FIG. 6) and the desired number of bends in each revolution of the helix.

Figure 6:
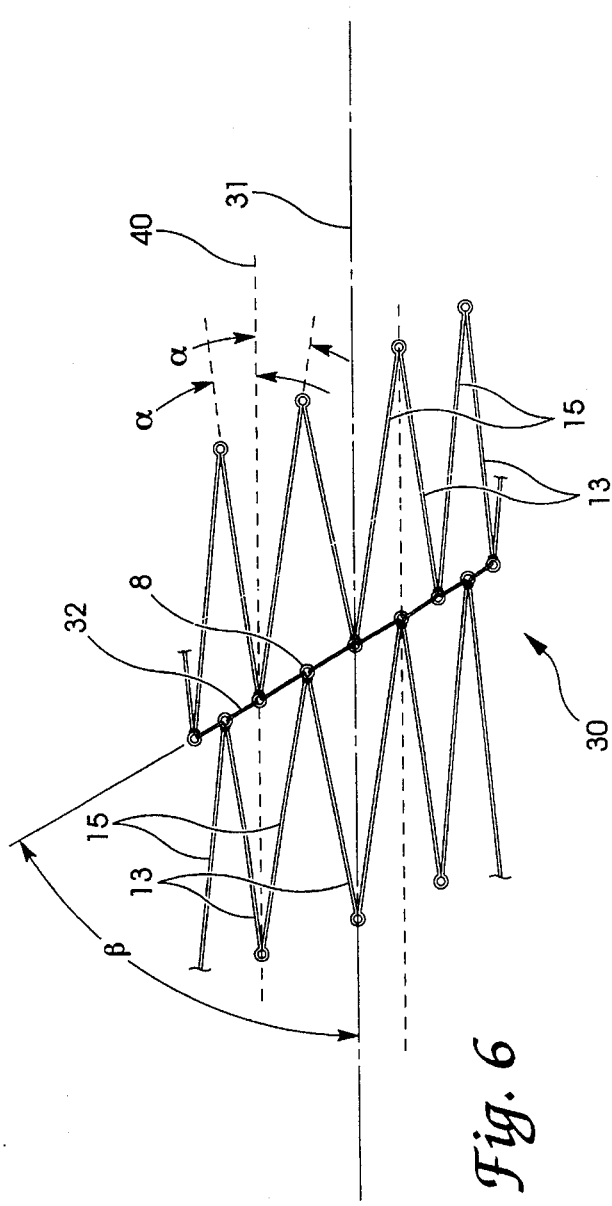
FIG. 6 is an enlarged view of a portion stent of FIG. 3.

Another important aspect of the present invention is illustrated in FIG. 6, which is an enlarged view of a portion of the stent shown in FIG. 3. The body of stent 30 includes a series of alternating short and long sections, 13 and 15 respectively. A bend 8 connects each pair of short and long sections 13 and 15. Each bend 8 defines an angle 2α which can be bisected by a bisector 40. These short and long sections are arranged in such a way that bisector 40 is parallel to the central axis 31 of the stent. This allows the stent to be radially compressed without unnecessary distortion.

FIG. 2 shows an enlarged view of one end of the zigzag pattern. End 6 of the wire is bent to form a closed eye portion 20. Eye 20 is preferably kept closed by the application of the small amount of solder to the end 6 of the wire after it has been bent into a small loop. Each of the bends 8 of the zigzag pattern are bent to include a small eye portion designated as 21 and 23 in FIG. 2, respectively. Eye 21 includes a small amount of solder 22 which renders eye 21 closed. Eye 23 includes no solder and is left open. In the preferred embodiment, all the end bends 36 shown in FIG. 3 are formed and soldered similar to closed eye 21 so that the filament which is tied to each eye is less likely to escape. The bends 8 which define the helix can be either in the form of a closed eye, as in eye 21, or open as in eye 23.

Figure 7:
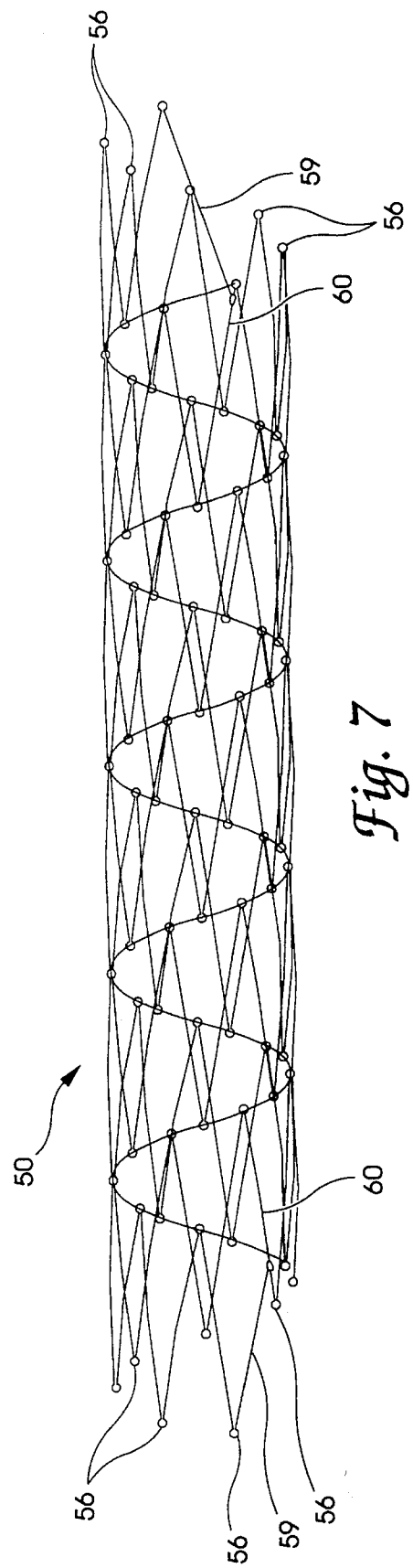
FIG. 7 is a side elevation of another embodiment of the present invention in its expanded shape.

FIG. 7 shows another embodiment of the present invention. Stent 50 is similar to stent 30 discussed previously except in this case, end bends 56 are not interconnected to one another. Stent 50 is also different in the way that the respective ends of the wire are connected to the remainder of the stent. In the case of stent 50, the end sections 59 are soldered to an adjacent elongated section 60. On the other hand, ends 6 of stent 30 shown in FIG. 3 are tied into the helix between two adjacent bends 8 of the helix. It is to be understood that the means employed for connecting the ends of the wire into the finished stent can be varied without departing from the intended scope of the present invention. What is important is that the end sections of the wire be secured to the stent in such a way that they are not left to dangle freely so as to interfere with the stents expansion or present a risk of unnecessary trauma to the vascular wall of the patient.

Because of the helical pattern of the present invention, the bends of the stent are distributed along its length rather than being concentrated at certain locations along the length of the stent. Thus the spiral stent is able to define a smaller compressed shape than either conventional zigzag stents or modified zigzag stents in which the bends are all located at a single location along the length of the stent. It is also believed that the helical pattern allows the elongated stent to more uniformly accommodate curves in the vascular system of a patient. The helical structure also produces a more uniform radial expansile force along the length of the stent. Finally, the spiral stents of the present invention are more reliable in maintaining their position within a patient.

Figure 8:
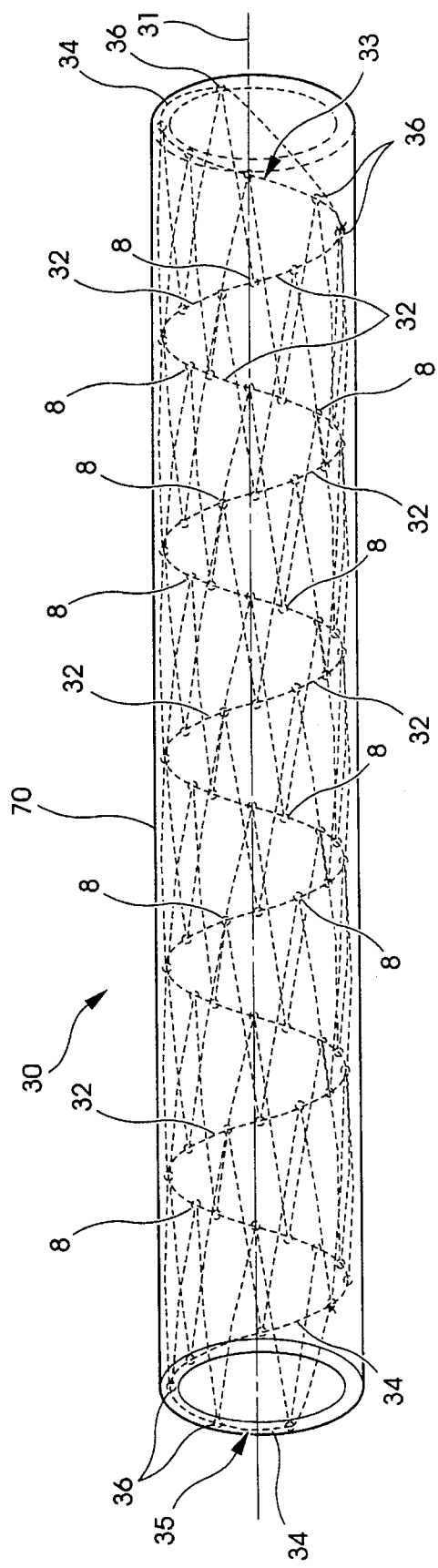
FIG. 8 is a side elevation of another embodiment of the present invention incorporating a flexible sleeve.

Referring now to FIG. 8, one variation of the present invention might include a flexible sleeve 70 attached to the outer or inner surface of the stent such that an elongated stent could be used to repair an aneurysm. In this use, the end portions of the sleeved stent would contact the wall of the vessel, and the body of the sleeve 70 stent would span the aneurysm. The sleeve could be made from nylon, plastic or any other biocompatible material. If the sleeve 70 were made of plastic, the stent could be attached to the sleeve 70 by embedding the stent in the plastic. If made of nylon, the sleeve 70 could be attached to the stent by a plurality of stitches. It is to be understood that the means for attaching the stent to the sleeve 70 could be varied depending upon the sleeve material, and other factors, without diverging from the intended scope of the present invention. Furthermore, the sleeve 70 itself could be used as the means for interconnecting adjacent bends of the helix.

Another variation of the present invention contemplates varying the lengths of the wire sections in the zigzag pattern. For instance, shortening the longest section and lengthening the shortest sections could be employed to even out the forces near the ends of the stent as well as to make square ends. Another variation would be to arrange the zigzag pattern in such a way that the tubular shape defined by the stent has a diameter that varies along the length of the stent. In other words, a stent could be made hour-glass in shape, or have a steadily tapered inner diameter, or even a combination of the two. This could be accomplished by varying along the length of the stent the number of bends in each revolution of the helix. In these variations, the helical pattern would be maintained but would be irregularly shaped along the length of the stent. Still another variation would be to vary the lengths of the wire sections within the body of the stent to create curves or to vary the expansile force along the length of the stent.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

We claim:

1. A self-expanding stent comprising:

a wire bent into an elongated zigzag pattern having a plurality of substantially straight wire sections separating a plurality of bends;

said zigzag pattern being helically wound about a central axis to define a tubular shape such that a majority of said plurality of bends are disposed in a helix;

means for interconnecting adjacent bends of said helix; and said stent having a radially compressed state such that said straight wire sections and said bends are tightly packed around said central axis, whereby said stent resiliently self-expands to assume said tubular shape when released from said compressed state.

2. The self-expanding stent of claim 1 wherein said tubular shape defines a length and a diameter that varies along said length.

3. The self expanding stent of claim 1 further comprising a flexible sleeve open at both ends and attached to said stent, said flexible sleeve being supported by said stent.

4. The self expanding stent of claim 1 wherein each of said bends disposed in said helix defines an angle, and a bisector of each said angle is substantially parallel to said central axis.

5. A self-expanding stent comprising:

a wire bent into an elongated zigzag pattern having a plurality of substantially straight wire sections separating a plurality of bends;

said zigzag pattern being helically wound about a central axis to define a tubular shape such that a majority of said plurality of bends are disposed in a helix;

means for interconnecting adjacent bends of said helix, wherein said means for interconnecting is a filament, said filament preventing said stent from expanding radially beyond a tubular shape of predetermined size; and said stent having a radially compressed state such that said straight wire sections and said bends are tightly packed around said central axis, whereby said stent resiliently self-expands to assume said tubular shape when released from said compressed state.

6. The self-expanding stent of claim 5 wherein said stent has two ends, each said end being defined by a plurality of end bends, adjacent said end bends being interconnected by a filament.

7. The self-expanding stent of claim 6 wherein each of said plurality of bends is bent to include an eye portion, said filament being tied to each said eye portion.

8. The self-expanding stent of claim 7 wherein at least two of said eye portions are closed.

9. The self-expanding stent of claim 8 wherein said wire has first and second ends each formed into defining a closed eye portion, said first and second ends being disposed in said helix and interconnected to two adjacent said bends in said helix.

10. The self-expanding stent of claim 5 wherein said wire has first and second ends, each being soldered to a different one of said plurality of straight wire sections.

\* \* \* \* \*

UNITED STATES PATENT AND TRADEMARK OFFICE
CERTIFICATE OF CORRECTION

PATENT NO. : 5,507,767

DATED : April 16, 1996

INVENTOR(S) : Munehiro Maeda; Hans A. Timmermans; Barry T. Uchida; Josef Rosch

It is certified that error appears in the above-identified patent and that said Letters Patent is hereby corrected as shown below:

Column 3, line 37, please insert --For-- in front of "instance,".

Signed and Sealed this

Thirtieth Day of July, 1996

Attest:

BRUCE LEHMAN

Attesting Officer

Commissioner of Patents and Trademarks